United States Patent [19]

Gottwald et al.

[11] Patent Number: 4,861,592

[45] Date of Patent: Aug. 29, 1989

[54] PHARMACEUTICAL COMPOSITIONS

[75] Inventors: Eberhard F. Gottwald, Bovenden; Horst M. Machoczek, Gleichen-Reinhausen, both of Fed. Rep. of Germany

[73] Assignee: Smith Kline Dauelsberg GmbH, Göttingen, Fed. Rep. of Germany

[21] Appl. No.: 57,578

[22] Filed: Jun. 2, 1987

Related U.S. Application Data

[63] Continuation of Ser. No. 744,096, Jun. 6, 1985, abandoned.

[51] Int. Cl.$^4$ .................... A61K 33/10; A61K 33/08; A61K 59/06; A61K 31/415
[52] U.S. Cl. ..................... 424/687; 424/690; 424/692; 424/686; 514/400; 514/975; 514/785; 514/974
[58] Field of Search ............... 514/400, 974, 785, 975, 514/156, 157, 158

[56] References Cited

U.S. PATENT DOCUMENTS 4,427,681  1/1984  Munshi ................................ 424/260

FOREIGN PATENT DOCUMENTS 0040489  11/1981  European Pat. Off. .
164122  12/1981  Japan .
1550359  8/1979  United Kingdom .

OTHER PUBLICATIONS

*Unlisted Drugs,* vol. 31, No. 1, Jan. 1979 (Chatham, U.S.) p. 7, See p. 7g Gastromet.
*Unlisted Drugs,* vol. 31, No. 1, Jan. (Chatham, U.S.) p. 13, See p. 13a, Ulcomet.

*Primary Examiner*—Frederick E. Waddell
*Attorney, Agent, or Firm*—Joseph A. Marlino; Stuart R. Suter; Alan D. Lourie

[57] ABSTRACT

A pharmaceutical composition suitable for oral administration comprising particulate cimetidine suspended in an aqueous phase containing a buffer which maintains the pH at greater than 7 and a suspending agent.

8 Claims, No Drawings

PHARMACEUTICAL COMPOSITIONS

This is a continuation of application of Ser. No. 744,096 now abandoned filed June 6, 1985.

This invention relates to pharmaceutical compositions suitable for oral administration which contain cimetidine and which have an improved flavour.

Cimetidine is a histamine H2-antagonist. It has been described in U.K. Patent Specification No. 1,397,436. Cimetidine has been shown to be useful in the treatment of duodenal, gastric, recurrent and stomal ulceration, and reflux oesophagitis and in the management of patients who are at high risk from hemorrhage of the upper gastrointestinal tract. Cimetidine has a pronounced bitter taste.

According to the present invention there is provided a pharmaceutical composition suitable for oral administration comprising particulate cimetidine dispersed in an aqueous phase containing a buffer that maintains the suspension at a pH greater than 7, and a suspending agent.

The advantage of the compositions of this invention is that they have a relatively less bitter taste than unbuffered suspensions.

Preferably the pH of the suspension is in the range pH 7.2–7.8.

In this specification, the expression "buffer" is used in a broad sense and means a salt of an acid that is partially dissociated in aqueous solution and that is capable of maintaining the pH of saliva in the alkaline range. The salt can be a mixture of salts. Examples of suitable buffers include disodium phosphate, sodium citrate, sodium fumarate, sodium acetate, sodium ascorbate, sodium glucuronate, and sodium gluconate.

Preferably the buffer is sodium citrate.

Preferably the concentration of the buffer is 2 to 50 micromolar, especially from 2 to 10 micromolar, and in particular it is 5 micromolar.

The composition also contains one or more suspending agents to keep the particulate cimetidine in suspension. Examples of suspending agents include microcrystalline cellulose and cellulose derivatives for example methylcellulose, and carboxymethylcellulose salts particularly sodium carboxymethylcellulose.

One particular suspending agent containing microcrystalline cellulose is Avicel RC 581.

Optionally the suspension also contains a suspension stabilizer for example a salt of a $C_{18}$–$C_{24}$ carboxylic acid, in particular arachidic acid salts and especially calcium arachinate.

Viscosity has an effect upon the taste of the suspension. Generally, as the viscosity of the suspension is increased, the taste becomes less bitter. It has been found that for the suspensions of the present invention, where the viscosity is greater than 1,500 mPa.s. an additional improvement in taste is obtained. In practice the viscosity of the suspension is not greater than 8,000 mPa.s.

Preferably the viscosity is at least 2,500 mPa.s. Preferably it is not greater than 6,000 mPa.s. and in particular it is in the range 3–4,000 mPa.s.

The suspending agents and suspension stabilizers referred to above have a marginal effect on the viscosity of the suspension but in order to obtain the viscosities referred to above it is preferable to increase the viscosity by including a thickening agent.

Thickening agents include medium and high viscosity cellulose derivatives. A medium viscosity cellulose derivative is one where the viscosity of a 2% w/v solution at 25° C. is at least 200 mPa.s. A high viscosity cellulose derivative is one where the viscosity of a 1% w/v solution at 25° C. s at least 1,000 mPa.s.

Preferably the thickening agent is a sodium carboxymethylcellulose as these cellulose derivatives have a greater effect on masking the bitter taste of cimetidine than do neutral cellulose derivatives for example methylcellulose of comparable viscosity.

Preferably the sodium carboxymethylcellulose is a high viscosity cellulose derivative. One particular sodium carboxymethylcellulose for use in this invention is Blanose 7 HF.

The precise quantity of the thickening agent to be added to the suspension can be established empirically and depends upon the amounts and thickening effect of the other ingredients in the suspension.

The suspension can contain other ingredients which improve its taste for example sweeteners in particular sugar alcohols especially sorbitol and xylitol, bitter taste maskers for example sodium chloride, taste masking flavours for example contramarum and flavouring agents.

A sugar alcohol sweetener for example sorbitol may not be sufficiently sweet for some palates. In this case additional sweeteners, for example sodium cyclamate, sodium saccharinate, aspartame and ammonium glycyrrhizinate can be added.

The particle size of the cimetidine is selected so as to obtain a pleasant mouth feel. This can be achieved using cimetidine where the average particle size for 90% by the Coulter counter method is less than 100 $\mu$m. Preferably the average particle size for 90% is less than 80 $\mu$m.

The quantity of cimetidine in the suspension is at least 100 mg per unit dose and preferably 200 mg. Convenient unit doses are from 5 to 10 g of suspension; a particularly convenient unit dose is 7 g. The suspension can be packaged in a unit dosage form for example in sachets.

The composition of this invention can optionally contain an antacid. An antacid is a pharmaceutically acceptable basic material of sufficient neutralising capacity to neutralise stomach acid. Suitable antacids are aluminium hydroxide, magnesium hydroxide, magnesium carbonate, calcium carbonate and co-dried gels for example aluminium hydroxide-magnesium carbonate co-dried gel. The amount of antacid is such that a unit dose contains 10–30 milliequivalents.

Preferably the antacid is calcium cabonate.

Where an antacid is present, the pH of the suspension will be greater than pH 8, and preferably the suspension has a pH in the range pH 8.5–9.5.

The compositions of the invention can be prepared by mixing cimetidine with the buffer and any other ingredients to be included to form a suspension. Preferably the mixing is done in a closed system to prevent contamination and at reduced pressure to prevent foam formation.

The following Examples illustrate the invention. In the Examples, the amounts given for the ingredients are the amounts in a single dose.

EXAMPLE 1

Autoclaved high viscosity sodium carboxymethylcellulose (10 mg; sold under the trade name Blanose 7 HF) was dissolved in aqueous sorbitol solution (70% by weight; 6914 mg) (the sorbitol-cellulose solution). To the sorbitol-cellulose solution was added cimetidine (200 mg; average particle size 90% less than 80 μm by Coulter counter), sorbic acid odour masking agent (2 mg), microcrystalline cellulose-sodium carboxymethylcellulose suspending agent (350 mg; sold under the trade name Avicel RC 581), calcium arachinate suspension stabilizer (200 mg), trisodium citrate dihydrate (10 mg) and sodium chloride (10 mg). The vessel containing the ingredients was evacuated and the ingredients were mixed in vacuo until homogeneous. To this mixture was added a peppermint-chocolate flavour mixture (39 mg) and the mixture so obtained was mixed until homogeneous. The product so obtained was a viscous syrup with a viscosity in the range 3-4,000 mPa.s. and pH 7.2 containing 200 mg cimetidine in approximately 7 ml of fluid.

EXAMPLE 2

A sorbitol-cellulose solution was made by dissolving autoclaved high viscosity sodium carboxymethylcellulose (30 mg; sold under the trade name Blanose 7 HF) in water (4.1 ml) to sorbitol (2.75 g). Alternatively, the sorbitol-cellulose solution can be made by dissolving sodium carboxymethylcellulose (30 mg; sold under the trade name Blanose 7 HF) directly in aqueous sorbitol solution (6.875 g, 40% by weight). This sorbitol-cellulose solution was substituted for the sorbitol-cellulose solution in the method of Example 1 and the other ingredients were mixed in the amounts and in the way described in Example 1, except that the amount of trisodium citrate dihydrate was increased (150 mg) to improve taste. The product so obtained was a viscous syrup with a viscosity in the range 3-4,000 mPa.s. and pH 7.8.

EXAMPLE 3

A xylitol-cellulose solution was made by dissolving autoclaved high viscosity sodium carboxymethylcellulose (30 mg; sold under the trade name Blanose 7 HF) in water (4.1 ml) and to this was added xylitol (2.75 g). Alternatively, the xylitol-cellulose solution can be made by dissolving sodium carboxymethylcellulose (30 mg; sold under the trade name Blanose 7HF) directly in aqueous xylitol solution (6.875 g, 40% by weight). This xylitol-cellulose solution was substituted for the sorbitol-cellulose solution in the method of Examples 1 and 2 and the other ingredients were mixed in the amounts and in the way described in Examples 1 and 2. The products so obtained were viscous syrups with viscosities in the range 2-3,000 mPa.s. and pH 7.2 or 7.8 depending on whether Example 1 or Example 2 was followed.

EXAMPLE 4

Autoclaved high viscosity sodium carboxymethylcellulose (7.5 mg; sold under the trade name Blanose 7 HF) was dissolved in aqueous sorbitol solution (70% by weight; 8.434 g) (the sorbitol-cellulose solution). To the sorbitol-cellulose solution was added cimetidine (100 mg) average particle size 90% less than 80 μm by Coulter counter), sorbic acid (2 mg), microcrystalline cellulose-sodium carboxymethylcellulose suspending agent (350 mg; sold under the trade name Avicel RC 581), calcium-arachinate suspension stabilizer (100 mg), trisodium citrate dihydrate (20 mg), sodium saccharinate (2 mg), FMA-11 aluminium hydroxide-magnesium carbonate co-dried gel (300 mg) and magnesium hydroxide paste (30% w/w; 666.67 mg). The vessel containing the ingredients was evacuated and the ingredients were mixed in vacuo until homogeneous. To this mixture was added an orange flavour (2.5 mg) and taste masking flavour (contramarum; 0.5 mg). The mixture so obtained was mixed until homogeneous. The product so obtained was a viscous syrup with a viscosity in the range 3-4,000 mPa.s. and pH 9.3 and contained 100 mg cimetidine in about 9 ml of fluid.

EXAMPLE 5

Autoclaved high viscosity sodium carboxymethylcellulose (30 mg, sold under the trade name Blanose 7 HF) was dissolved in aqueous sorbitol solution (40% by weight, 8.434 g). This sorbitol-cellulose solution was substituted for the sorbitol-cellulose solution in the method of Example 4 and the other ingredients were mixed in the same amounts and in the same way as described in Example 4. The product so obtained was a viscous syrup with a viscosity in the range 3-4,000 mPa.s. and pH 8.9.

EXAMPLE 6

Autoclaved high viscosity sodium carboxymethylcellulose (25 mg, sold under the trade name Blanose 7 HF) was dissolved in aqueous sorbitol solution (40% by weight, 4.400 g) (the sorbitol-cellulose solution). To the sorbitol-cellulose solution was added cimetidine (100 mg average particle size 90% less than 80 μm by Coulter counter), sorbic acid (2 mg), microcrystalline cellulose sodium-carboxymethylcellulose suspending agent (150 mg, sold under the trade name Avicel RC 581), calcium arachinate suspension stabilizer (50 mg), trisodium citrate dihydrate (20 mg), potassium glycyrrhizinate (10 mg), sodium cyclamate (10 mg), FMA-11 aluminium hydroxide-magnesium carbonate co-dried gel (300 mg), and magnesium hydroxide paste (30% w/w, 666.67 mg). The vessel containing the ingredients was evacuated and the ingredients were mixed in vacuo until homogeneous. To this mixture was added a peppermint-chocolate-contramarum flavour mixture (30 mg) and mixed until homogeneous. The product so obtained was a viscous syrup with a viscosity in the range 3-4,000 mPa.s. and pH 9.0.

EXAMPLE 7

Autoclaved high viscosity sodium carboxymethylcellulose (25 mg, sold under the trade name Blanose 7 HF) was dissolved in aqueous sorbitol solution (40% by weight, 4.400 g) (the sorbitol-cellulose solution). To the sorbitol-cellulose solution was added cimetidine (100 mg average particle size 90% less than 80 μm by Coulter counter), sorbic acid (2 mg), microcrystalline cellulose sodium-carboxymethylcellulose suspending agent (150 mg, sold under the trade name Avicel RC 581), calcium arachinate suspension stabilizer (50 mg), trisodium citrate dihydrate (20 mg), sodium saccharinate (1.5 mg), sodium cyclamate (10 mg), FMA-11 (300 mg) aluminium hydroxide-magnesium carbonate co-dried gel), and magnesium hydroxide paste (30% w/w, 666.67 mg). The vessel containing the ingredients was evacuated and the ingredients were mixed in vacuo until homogeneous. To this mixture was added a peppermint-chocolate-contramarum flavour mixture (30 mg) and mixed until homogeneous. The product so obtained was a viscous syrup with a viscosity in the range 3-4,000 mPa.s. and pH 8.9.

EXAMPLE 8

A mixture of high viscous sodium-carboxymethylcellulose (20 mg, sold under the trade name Blanose 7 HF), hydroxypropylmethylcellulose (20 mg, sold under the trade name Methocel E 5) and calcium arachinate (20 mg) are autoclaved and suspended in a solution of sodium chloride (10 mg) and sorbic acid (3 mg), in water (2.01 g). When the mixture so obtained had formed a gel (after about 12 hours), a solution of 70% sorbitol (2.684 g), magnesium hydroxide (50 mg), calcium carbonate (500 mg), microcrystalline cellulose-sodium carboxymethylcellulose suspending agent (200 mg, sold under the trade name Avicel RC 581), calcium arachinate (130 mg) potassium glycyrrhizinate (5 mg) and cimetidine (100 mg) were added with vigorous stirring. This suspension was passed through a vacuum degasser and mixed with a flavouring agent. The product so obtained was a viscuous syrup with a viscosity in the range 2–4,000 mPa.s. and pH 7.8.

EXAMPLE 9

Sodium-carboxymethylcellulose (40 mg, sold under the trade name Blanose 7 HF) and hydroxypropylcellulose (40 mg, sold under the trade name Methocel E 5) were added with constant stirring to a solution of trisodium citrate dihydrate (150 mg), sorbic acid (5 mg), sodium saccharin (0.2 mg) and sodium cyclamate (1 mg) in water (2875 mg). The stirring was continued until a mixture of even consistency was obtained. The mixture formed a gel within 12 hrs.

After the gel had formed, the following were added and mixed so as to obtain an even distribution: calcium arachinate suspension stabilizer (150 mg); microcrystalline cellulose-sodium carboxymethylcellulose suspending agent (350 mg; sold under the trade name Avicel RC 581), and cimetidine (200 mg; average particle size 90% less than 80 μm by Coulter counter). The mixture so obtained was diluted with aqueous sorbitol solution (3.82 g; 70%) and after passing it through a vacuum degasser a flavouring agent was added. The product so obtained was a viscous syrup with a viscosity in the range 2–4,000 mPa.s. and pH 7.8.

We claim:

1. A pharmaceutical composition suitable for oral administration comprising from about 100 mg. to about 200 mg of particulate cimetidine per unit dose suspended in an aqueous phase containing a buffer which maintains the pH at from greater than 7.0 to 9.5, a suspending agent and/or a thickening agent, said composition having a viscosity in the range of from greater than 1,500 m Pa.s. to 8,000 m Pa.s.

2. A composition as claimed in claim 1 where the buffer is trisodium citrate.

3. A pharmaceutical composition for oral administration comprising an effective histamine $H_2$-antagonist amount of particulate cimetidine suspended in an aqueous phase containing a buffer which maintains the pH at from about 7.0 to 9.5, a suspending agent and/or a thickening agent, and a pharmaceutically acceptable salt of a $C_{18}$–$C_{24}$ carboxylic acid as a suspension stabilizer, said composition having a viscosity in the range of from greater than 1,500 m Pa.s. to 8,000 m Pa.s.

4. A composition according to claim 3 wherein the $C_{18}$–$C_{24}$ carboxylic acid salt is an arachidic acid salt.

5. A composition according to claim 4 wherein the arachidic acid salt is calcium arachinate.

6. A composition according to claim 3 having a PH of from 7.2 to 7.8.

7. A compostion according to claim 3 containing an antacid.

8. The composition according to claim 7 having a pH of from 8.5 to 9.5.

* * * * *